United States Patent [19]
Leclerc

[11] Patent Number: 5,616,214
[45] Date of Patent: Apr. 1, 1997

[54] DETERMINATION OF SODIUM SULFIDE AND SULFIDITY IN GREEN LIQUORS AND SMELT SOLUTIONS

[75] Inventor: Denys F. Leclerc, Surrey, Canada

[73] Assignee: Pulp and Paper Research Institute of Canada, Pointe-Claire, Canada

[21] Appl. No.: 526,873

[22] Filed: Sep. 12, 1995

[51] Int. Cl.$^6$ .................................................. D21C 7/14
[52] U.S. Cl. ........................... 162/49; 162/238; 162/263; 162/DIG. 10
[58] Field of Search ............................. 162/49, 263, 238, 162/DIG. 10; 250/339.11, 339.12, 339.09

[56] References Cited

U.S. PATENT DOCUMENTS

| | | | |
|---|---|---|---|
| 4,717,672 | 1/1988 | Fleming et al. | 436/55 |
| 4,743,339 | 5/1988 | Faix et al. | 162/49 |
| 5,104,485 | 4/1992 | Weyer | 162/49 |
| 5,282,931 | 2/1994 | LeClerc et al. | 162/49 |
| 5,364,502 | 11/1994 | Leclerc et al. . | |
| 5,378,320 | 1/1995 | Leclerc et al. . | |

FOREIGN PATENT DOCUMENTS

| | | |
|---|---|---|
| WO91/17305 | 11/1991 | WIPO . |
| WO93/14390 | 7/1993 | WIPO . |

OTHER PUBLICATIONS

Haaland D. M. et al., "Partial Least–Squares Methods for Spectral Analyses 1. Relation to Other Quantitative Calibration Methods and the Extraction of Qualitative Information" Analytical Chemistry, vol. 60 No. 11:1193–1202 Jun. 1, 1988.

Haaland D. M. et al., "Partial Least–Squares Methods for Spectral Analyses. 2. Application to Simulated and Glass Spectral Data" Analytical Chemistry, vol. 60, No. 11:1202–1208 Jun. 1, 1988.

Banfill et al. "Reduced Emissions Change Chemical Balances in Bleached Kraft Pulp Mills" Pulp & Paper Canada Mag. 1993 94(1) T21–t24.

D.C. Taflin "Estimating the Impact on Makeup & the Liquor Loop . . . " Proc. 1991 Tappi Pulp Conf. Orlando FL. pp. 821–827, Tappi Press, Atlanta, GA.

D. Peramunage et al. "Activity & Spectroscopic Analysis of Concentrated . . . " Anal. Chem. 1994, vol. 66, No. 3, 378–383.

Paulonis et al. "Kraft White & Green Liquor Composition Analysis. Part I: Discrete Sample Analyser. " J. Pulp Paper Sci. 1994, vol. 20 No. 9, J254–258.

Salomon D R "Applications of Capillary Ion Electrophoresis in the Pulp & Paper Industry" J. Chromatogr. 1992 602(1–2) 219–225

D.R. Salomon et al. "Rapid Ion Monitoring of Kraft Process Liquors by Capillary Electrophoresis" Process Control & Quality, 1992 3(1–4) 219–27.

(List continued on next page.)

*Primary Examiner*—Donald E. Czaja
*Assistant Examiner*—Steven B. Leavitt
*Attorney, Agent, or Firm*—Swabey Ogilvy Renault

[57] ABSTRACT

A rapid method is provided for the on-line determination of sodium sulfide concentration and/or percent sulfidity in green liquors or smelt solutions used for the production of either kraft or sulfite pulp. The method eliminates manual sampling, and the need for frequent equipment maintenance. The method includes the steps of withdrawing samples of a smelt solution or green liquor from the kraft or sulfite manufacturing process, subjecting the samples to near-infrared spectrophotometry over a predetermined range of wave numbers so as to produce absorbance measurements relative to a reference spectrum of either water or a caustic soda-sodium carbonate solution, determining the absorbance shown by different combinations of sodium sulfide, sodium hydroxide, sodium carbonate and sodium chloride concentrations, correlating by multivariate calibration the relationships between the absorbance measurements of unknown samples and the absorbance shown by different combinations of sodium sulfide, sodium hydroxide, sodium carbonate and sodium chloride so that the amount of sodium sulfide and/or the percent sulfidity can be accurately determined for any levels of TTA or chloride present in the liquor.

20 Claims, 15 Drawing Sheets

OTHER PUBLICATIONS

P. Isaak et al. "Stickiness of Fireside Deposits in Kraft Recovery Units. Part II. The Effects of Potassiium and Surface Treatment. " J. Pulp Paper Sci. 1987, 13(5), J154.

A.J. Michell "Kappa Number Determination in Kraft Pulping by FTIR Spectroscopic Measurements on Spent Liquors" Tappi Journal 1990, 73(4), 235.

O. Faix et al. "Continuous Process Control of Pulping by FTIR Spectroscopy" Tappi Proceedings, 1989 Wood & Pulping Chemistry Symposium, Raleigh NC.

D.F. Leclerc et al. "Rapid Determination of Effective Alkali and Dead Load Concentrations in Kraft . . . " J. Pulp Paper Sci. 1995, 21(7), J231.

Watson et al. "On–line Analysis of Caustic Streams by Near Infrared Spectroscopy" Spectroscopy, 1990 2(1) 44.

T. Hirschfeld "Salinity Determination Using NIRA" Appl. Spectroscopy 1985 39(4), 740–1.

Grant et al. "Simultaneous Determination of Sodium Hydroxide, Sodium Carbonate & Sodium Chloride . . . " Analyst, 1989, 114(7), 819–22.

Haaland D M et al. "Partial Least Squares Methods for Spectral Analyses 1. Relation to Other . . . " Anal. Chem. 60(10):1193–1202, 1988.

J. Lin et al. "Near IR Spectroscopic Determination of NaCl in Aqueous Solution" Appl. Spectrosc. 1992 46(12), 1809–15.

J. Lin et al. "Near IR Spectroscopic Measurement of Seawater Salinity" Environ. Sci. Technol. 1993, 27(8), 1611–6.

J. Lin et al. "Near–IR Fiber Optic Probe for Electrolytes in Aqueous Solution" Anal. Chem. 1993, 65(3), 287–92.

J. Lin et al. "Near IR Fiber Optic Temperature Sensor" Appl. Spectrosc. 1993 47(1),62–8.

J. Lin et al. "Spectroscopic Measurement of NaCl and Seawater Salinity in the Near IR Region . . . " Appl. Spectrosc. 1993. (47(2), 239–41.

M.K. Phelan et al. "Measurement of Caustic Brine Solutions by Spectroscopic Detection of the Hydroxide . . . " Anal. Chem. 1989, 61(13), 1419–24.

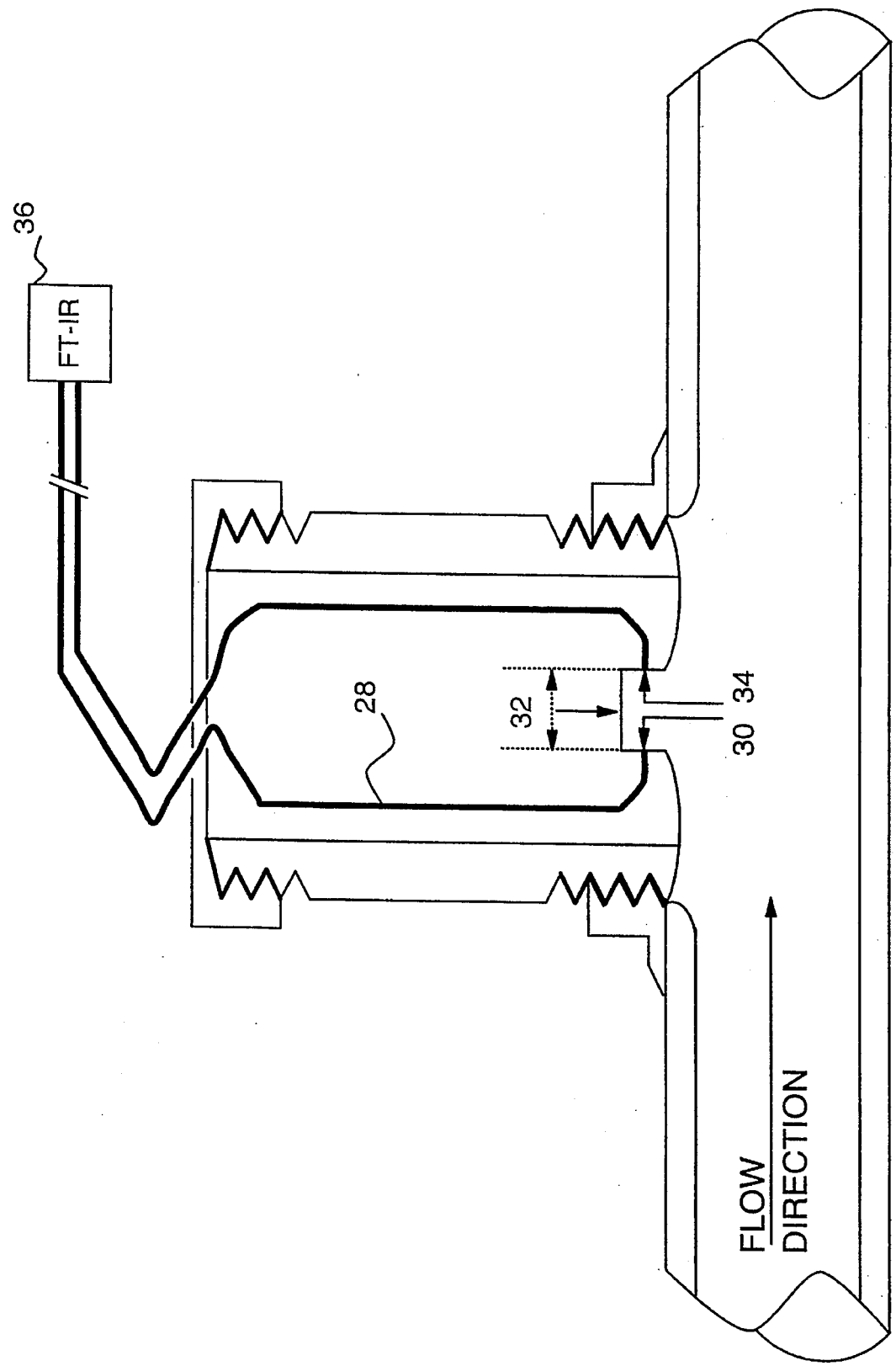

| | | |
|---|---|---|
| 1 = (5, 5, 40, 35) | 9 = (20, 20, 40, 5) | 17 = (20, 5, 60, 15) |
| 2 = (20, 5, 40, 25) | 10 = (5, 26, 40, 5) | 18 = (35, 5, 60, 5) |
| 3 = (5, 12, 40, 25) | 11 = (5, 5, 60, 25) | 19 = (20, 5, 80, 5) |
| 4 = (35, 5, 40, 15) | 12 = (5, 12, 60, 15) | 20 = (20, 12, 60, 5) |
| 5 = (20, 12, 40, 15) | 13 = (5, 5, 80, 15) | 21 = (10, 7.3, 80, 8.3) |
| 6 = (5, 20, 40, 15) | 14 = (5, 20, 60, 14) | 22 = (12.5, 8.5, 60, 15) |
| 7 = (50, 5, 40, 5) | 15 = (5, 12, 80, 5) | 23 = (12.5, 12, 60, 10) |
| 8 = (35, 12, 40, 5) | 16 = (5, 5, 100, 5) | 24 = (20, 8.5, 60, 10) |

DETERMINATION OF SODIUM SULFIDE AND SULFIDITY IN GREEN LIQUORS AND SMELT SOLUTIONS

BACKGROUND OF THE INVENTION i) Field of the Invention

This invention relates to a method for determining a sulfur concentration parameter in an aqueous pulp liquor, and to a cellulosic pulp manufacturing installation which employs the method; more especially the invention relates to an on-line method for determining sodium sulfide concentrations and optionally percent sulfidity during the recovery operation of a sulfate (kraft) or sulfite mill. The invention specifically relates to the application of near-infrared spectrometry for measuring the absorbance of smelt solutions or green liquors containing sulfide, hydroxide, carbonate and chloride ions.

ii) Description of Prior Art

Kraft pulping is performed by cooking wood chips in a highly alkaline white liquor which selectively dissolves lignin and releases the cellulosic fibers from their wood matrix. The two major chemicals in the white liquor are caustic soda and sodium sulfide. Caustic soda is a strong alkali. Sodium sulfide is also a strong alkali, readily hydrolysing in water to produce one mole of sodium hydroxide and one mole of sodium hydrosulfide for each mole of sodium sulfide. The total amount of sodium hydroxide is known as the effective alkali (EA). White liquor is produced by causticizing green liquor, which in turn is produced by dissolving a smelt of mainly sodium carbonate and sodium sulfide in water prior to removal of suspended solids, thereby producing a smelt solution which is then clarified so as to obtain green liquor. The smelt is produced in a chemical recovery furnace in which the organic content of black liquor is burned, black liquor being the liquor which remains after pulping with white liquor and depletion of sulfide and alkali therein. The sulfidity in green liquor is the amount of sodium sulfide in solution, divided by the total titratable alkali (TTA) which is the combined amount of sodium carbonate, sodium sulfide and sodium hydroxide. The sulfidity is usually expressed as a percentage (% S) which varies between 20 and 30 percent in green liquors. The reduction efficiency (RE) is defined as the amount (as $Na_2O$) of green-liquor sodium sulfide, divided by the combined amounts (as $Na_2O$) of sodium sulfide and sodium sulfate in the green liquor or smelt solution. The control of sodium sulfide, TTA and of non-process electrolytes such as sodium chloride and potassium chloride would have a beneficial impact on closed-cycle kraft-mill operations. For example, environmentally driven reduction of sulfur losses generally increases liquor sulfidity, thereby creating a sodium:sulfur imbalance that needs to be made up through the addition of caustic soda [Banfill and Bentley, Pulp Paper Mag. Can 1993 94(1) T21–T24; Taflin, Proc. 1991 TAPPI Pulp. Conf., Orlando Fla., pp. 821–827, TAPPI Press, Atlanta Ga.]. Another important need is the control of TTA in green liquor, which is most easily done by adding weak wash to the smelt dissolving tank. The value of the green-liquor TTA is important because it is correlated with liquor density. The density strongly influences the lime-mud settling rate in the recausticizing area, whereas the rate of the recausticizing reaction depends on green-liquor TTA. The ongoing development of modern chemical pulping processes has thus underscored the need for better control over all aspects of kraft-mill operations and more efficient use of all the chemicals involved in the process.

The on-line measurement of sulfide and/or sulfidity in concentrated liquors remains an important challenge in pulp and paper science. Traditional methods such as titration, gravimetry, and other, more modern, methods such as ion chromatography, voltammetry, atomic absorption spectroscopy and atomic emission spectroscopy have been used for the analysis of pulping liquors. Except for titration, none of these methods can be adapted for process analysis.

Automatic titration is thus the currently accepted method of choice for determining hydrosulfide on-line in kraft liquors. The basis of these systems involves the neutralization of alkali by strong acid during which the conductivity of the solution is measured so as to detect the titration equivalence point. These systems are complex, expensive and require extensive sample pretreatment. A major disadvantage of using titration for sulfide analysis is that $H_2S$ has to be vented into the atmosphere, a problem which raises serious environmental concerns. It is well known that hydrosulfide ions absorb very strongly in the ultraviolet at 214 nm [Holmquist and Jonsson: PCT Application WO 93/14390, "A Method of Determining the Concentration of Sulfide in Liquors and Smelt Solutions"; D. Peramunage, F. Forouzan, S. Litch, Anal. Chem. 1994, 66, 378–383; Paulonis et al.: PCT Application WO 91/17305, "Liquid Composition Analyser and Method"]. However, this absorption is so strong that a very small pathlength (less than 10 microns) is needed to get a measurable signal which yields a linear calibration curve [Paulonis et Krishnagopalan, "Kraft White and Green Liquor Composition Analysis. Part I: Discrete Sample Analyser", J. Pulp Paper Sci., 1994, 20(9), J254–J258]. A cell with such a pathlength is prone to plugging and hence not practical for on-line applications. Extensive (1:1000–1:10000) dilution is therefore practiced, thereby giving inaccurate results and increasing the risk of sulfide being oxidized. The dilution approach has also been used in techniques such as capillary zone electrophoresis [Salomon, D. R.; Romano, J. P. "Applications of Capillary Ion Analysis in the Pulp and Paper Industry", J. Chromatogr., 1992 602(1–2) 219–25; "Rapid Ion Monitoring of Kraft Process Liquors by Capillary Electrophoresis", Process Control Qual., 1992 3(1–4) 219–27]. Errors in sulfidity measurements exceeding 50% were reported. A method which does not need dilution is needed.

Potassium chloride promotes hot-spot corrosion on boiler tubes by reducing the melting-point temperature of sodium salts found on tube deposits [P. Isaak, H. N. Tran and D. W. Reeve; "Stickiness of Fireside Deposits in Kraft Recovery Units. Part II. The Effects of Potassium and Surface Treatment", J. Pulp Paper Sci., 1987, 13(5), J154]. If future practice evolves towards controlling potassium and chloride by purging saltcake through the precipitator catch, a means to measure potassium and sodium chloride will be needed because small temperature variations in the furnace strongly affect the quantity of potassium and chloride volatilizing into the catch. Components such as sodium chloride and potassium chloride are difficult to characterize and quantify in situ because of the lack of measurable spectroscopic absorption. The technique of choice is to perform infrequent off-line analysis of the liquors by cumbersome laboratory methods. Based on these laboratory results, certain remedial actions can be taken intermittently, such as increasing the precipitator catch discharge rate. A method for measuring chloride ions may also be needed.

The advent of modern Fourier transform infrared (FT-IR) techniques such as attenuated total reflectance (ATR) and near-infrared reflectance analysis (NIRA) has enabled researchers to determine the composition of either dissolved or suspended materials present in aqueous streams. Weyer proposes a near-infrared method [U.S. Pat. No. 5,104,485] for measuring the concentration of non-aqueous solids such as clay, calcium carbonate or titanium dioxide in a pulp slurry filtrate containing fines and non-aqueous constituents. However, the method cannot measure aqueous components such as sodium sulfide or sodium carbonate. An early example of the use of FT-IR ATR is given by Faix et al. who teach [U.S. Pat. No. 4,743,339] that a FT-IR ATR method can be used for determining lignin content in black liquor, thereby obtaining a correlation with the kappa number of the pulp. Michell in TAPPI Journal 1990, 73(4), 235 teaches a similar method for determining black-liquor lignin. Faix et al. also report [TAPPI Proceedings, 1989 Wood and Pulping Chemistry Symposium, Raleigh N.C.] that one is able to measure the consumption of sodium sulfite and the appearance of lignosulfonates during alkaline sulfite anthraquinone methanol (ASAM) pulping. Neither of these methods can be used for process control because of interferences from carbohydrates and uncertainties in the value of process variables such as liquor-to-wood ratio. Leclerc et al. [J. Pulp Paper Sci., 1995, 21(7), 231; U.S. Pat. Nos. 5,282,931, 5,364,502 and 5,378,320] teach that one can measure EA and dead-load components in kraft liquors with FT-IR ATR, and that one can use these measurements to control the operations of important process units involved in the manufacture of kraft pulp such as the digester, recausticizers and recovery boiler. Sodium sulfide, however, cannot be determined with the small pathlength afforded by the ATR method because of the weakness of its spectral absorption, thereby precluding any meaningful determination of TTA.

Recent advances in FT-IR instrumentation and software have made possible the use of the near-infrared region of the spectrum for determining aqueous components such as dissolved electrolytes. Each ionic species causes a unique and measurable modification to the water bands that is proportional to its concentration. Advantages over previous techniques include: no sample preparation, short measurement times and the possibility of using fiber-optic technology for real-time, in situ measurements. The use of near-infrared spectroscopy has been recently suggested by Watson and Baughman [Spectroscopy, 1990 2(1) 44], by Hirschfeld (Appl. Spectrosc. 1985, 39(4), 740–1), and by Grant et al. (Analyst, 1989, 114(7), 819–22) for measuring the concentration of dissolved electrolytes such as sodium hydroxide, carbonate and chloride concentrations in aqueous streams in the food and chemical industries. Watson and Baughman also reported that the presence of hydrosulfide did not generate any measurable spectral absorption, and thus did not interfere with the EA and carbonate measurements. Such a statement strongly suggests that one cannot measure sulfide and/or sulfidity by near-infrared spectrometry. On the other hand, temperature effects and interferences by other cations and anions can be modelled through the use of partial least-squares (PLS) multicomponent calibration techniques. PLS is a multicomponent calibration method which is well-known in the art [HAALAND, D. M. and THOMAS, E. V., Anal. Chem., 60(10):1193–1202 (1988); Anal. Chem., 60(10):1202–1208 (1988)]. This method enables one to build a spectral model which assumes that the absorbance produced by a species is linearly proportional to its concentration. Lin and Brown [Appl. Spectrosc. 1992, 46(12), 1809–15; Environ. Sci. Technol. 1993, 27(8), 1611–6; Anal. Chem., 1993, 65(3), 287–92; Appl. Spectrosc. 1993, 47(1), 62–8; Appl. Spectrosc. 1993, 47(2), 239–41] have shown that PLS calibration techniques can be very effective in resolving the simultaneous perturbative effects of several ions on the intensity of near-infrared water bands. Also, Phelan et al. [Anal. Chem., 1989, 61(13), 1419–24] have used PLS calibration to resolve the hydroxide ion spectrum near 970 nm.

A method which does not require sample preparation or reagents is strongly needed for the routine, on-line determination of sulfide and/or sulfidity in kraft or sulfite green liquors. However, the prior art [e.g., Watson and Baughman [ Spectroscopy, 1990 2 (1) 44] teaches against on-line infrared spectrophotometry for the on-line determination of sulfide and/or sulfidity in green liquors.

SUMMARY OF THE INVENTION

It is an object of this invention to provide a method for determining a sulfur concentration parameter of a pulp liquor.

It is a further object of the invention to provide a cellulosic pulp manufacturing installation.

In accordance with one aspect of the invention there is provided a method for determining a sulfur concentration parameter of a sulfide-containing aqueous pulp liquor comprising:

i) subjecting a sample of the aqueous pulp liquor to near infrared radiation at a predetermined wavelength region to produce a water absorbance peak value of said liquor, relative to a background spectrum, ii) comparing the peak value in i) with a calibration plot of corresponding peak values at said predetermined wavelength region, for a plurality of sulfide-containing aqueous pulp liquors of known sulfur concentration parameters, and iii) evaluating the sulfur concentration parameter of the sample from the comparison in ii).

In accordance with a particular embodiment of the invention there is provided a method for determining the concentration of sodium sulfide in green liquors and smelt solutions derived from the preparation of kraft or sulfite pulp wherein smelt is produced in a recovery furnace and fed to a smelt dissolving tank so as to form green liquor, which comprises the steps of:

withdrawing samples of a smelt solution or green liquor from the kraft or sulfite manufacturing process;

subjecting the undiluted samples to near-infrared spectrophotometry over the range of wave numbers from 4000 to 14000 $cm^{-1}$ so as to produce absorbance measurements relative to a reference spectrum of water or a caustic soda-sodium carbonate solution;

determining the absorbance shown by different mixture solutions of sodium sulfide, sodium hydroxide, sodium carbonate and sodium chloride of known concentrations;

correlating by multivariate calibration the relationships between the absorbance measurements of the samples and the absorbance shown by the different mixture solutions of known concentration, and evaluating from the correlation the amount of sodium sulfide for any level of total titratable alkali (TTA) or chloride present in the liquor.

In accordance with another aspect of the invention there is provided in a cellulosic pulp manufacturing installation having a green liquor preparation unit including a recovery furnace for chemicals derived from a pulp manufacture process, a green liquor generation tank and a smelt flow line for flow of a smelt of inorganic chemicals from said recovery furnace to said tank, the improvement comprising a sensing apparatus for determining a sulfur concentration parameter of said green liquor, said apparatus comprising a fiber optic sensor operatively connected to a source of near infrared radiation, a sample flow line from said tank, a sensing zone in said sample flow line for receiving near infrared radiation from said sensor, a spectrophotometer for recording absorbance spectra from said sensing zone, and comparator means for comparing the absorbance spectra from said sensing zone with a calibration of absorbance spectra for known concentration parameters and providing an evaluation of the concentration parameter of the sample.

DETAILED DESCRIPTION OF THE INVENTION

The method of the invention determines a sulfur concentration parameter of a pulp liquor.

This concentration parameter is, more particularly, a sulfide concentration or sulfidity.

In particular, the pulp liquor sample is fed from a green liquor preparation unit of a pulp manufacture process without dilution; in other words an undiluted sample of green liquor is taken for the investigation, the unit including a recovery furnace for chemicals derived from the pulp manufacture process. The green liquor is derived from a smelt of inorganic chemicals formed in the recovery furnace. The operation of the recovery furnace is controlled in response to the evaluation of the determined concentration parameter, so as to adjust the concentration parameter of the electrolyte in the green liquor.

In a particular embodiment, the method is employed to determine sulfidity on a TTA basis, of the green liquor; in this case, the caustic soda, sodium carbonate and chloride are also determined and the percent sulfidity is calculated from the data obtained; the combined concentration of caustic soda, sodium carbonate and chloride being determined by measuring the near infrared absorbance of undiluted green liquor.

The installation of the invention may particularly include control means for controlling operating parameters of the recovery furnace; the control means being operatively connected to the comparator means of the installation for adjustment of the operating parameters, responsive to the evaluation provided by the comparator means.

The present invention provides a rapid method for determining sodium sulfide and/or sulfidity in process liquors. This method overcomes the disadvantages previously discussed. The new analysis method largely eliminates the need for frequent equipment maintenance, sample pretreatment and the use of chemical reagents. High sample throughput will also allow many process streams to be multiplexed to a single analyzer through either the use of fiber optics or a multiple-stream sampling system.

The analysis method of the invention uses on-line near-infrared absorbance measurements obtained from transmission spectra, and relies on perturbations or shifts of water absorption bands by dissolved electrolytes. Each electrolyte generates a unique perturbation pattern which can be recognized and quantified by modern software methods. A pure-water or caustic soda-sodium carbonate absorbance spectra is first subtracted from the solution absorbance spectra so as to produce differential absorbance spectra which reflect not only the amount of sulfide, but also the variety of the other anionic species present in solution, i.e., hydroxide, carbonate and chloride, all of which interfere strongly with the sulfide determination. The differential absorbance spectrum of the liquor is measured along a predetermined spectral region. With the aid of a PLS calibration, the observed differential absorbance for each species is made to correlate directly with its actual concentration obtained from standard-method laboratory analysis. This correlation is generated by supplying spectra of mixtures to a training software which then develops a model for this spectral region and the liquor being used.

Although not necessary, it is generally preferable that the concentration of all ionic species be accounted for within a PLS calibration so that the sulfidity measurements are accurate and without bias, thereby creating a noise-free model that can be characterised with a small number of basis vectors. The basis vectors are then used by the model for characterising components in unknown samples. The chemical composition of the liquor is then calculated with the PLS model. The process samples are also analyzed with standard analytical methods (CPPA J.12) so as to establish a calibration set with the data obtained by infrared spectrophotometry. These calibration measurements are used in green liquors for monitoring the sulfidity and optionally measuring the accumulation of chloride salts in the liquor cycle during closed-cycle operations. Near-infrared sulfide measurements can also be used for improving the reduction of sulfate and thiosulfate to sulfide in the lower furnace of the recovery boiler. The application of this invention to pulp and paper liquors provides a method for determining sulfide and/or sulfidity that is faster, more reliable, and requires less maintenance than existing methods.

The on-line analytical procedure of the invention can also be used in green liquors for determining percent sulfidity which for green liquors is based on TTA, a parameter that also includes caustic soda and carbonate. The determination of chloride levels in green liquors is also necessary since the presence of these species interferes with the determination of sulfide and TTA. The PLS model can easily be made to directly quantify these other compounds. In summary, this new method can replace automatic titrators and conductivity sensors. It also gives much-needed information on the sulfide and/or sulfidity levels in green liquors.

In one embodiment the present invention provides a method for determining the sodium sulfide concentration and/or percent sulfidity of green liquor in either a kraft or sulfite pulp manufacturing process, comprising the steps of: withdrawing samples of either a green liquor or a smelt solution from the kraft or sulfite manufacturing process, subjecting the samples to near-infrared spectrophotometry over a predetermined range of wave numbers so as to either produce absorbance measurements relative to a reference spectrum of air, or produce the differential-absorbance measurements (calculated with respect to either a reference spectrum of water or caustic soda-sodium carbonate solution) shown by different combinations of sodium sulfide, sodium hydroxide, sodium carbonate and sodium chloride concentrations, correlating by multicomponent calibration the relationships between the absorbance measurements of unknown samples and the absorbance shown by different combinations of sodium sulfide, sodium hydroxide, sodium carbonate and sodium chloride so that the amount of sodium sulfide and/or the percent sulfidity present in the sample can be accurately determined for any levels of TTA and chloride present in the liquor.

BRIEF DESCRIPTION OF THE DRAWINGS

The invention is further explained by reference to the drawings which illustrate embodiments of the present invention in which:

FIG. 1B is a detail of a fiber optic sensor in FIG. 1A;

DESCRIPTION OF PREFERRED EMBODIMENTS WITH REFERENCE TO DRAWINGS

Figure 1A:
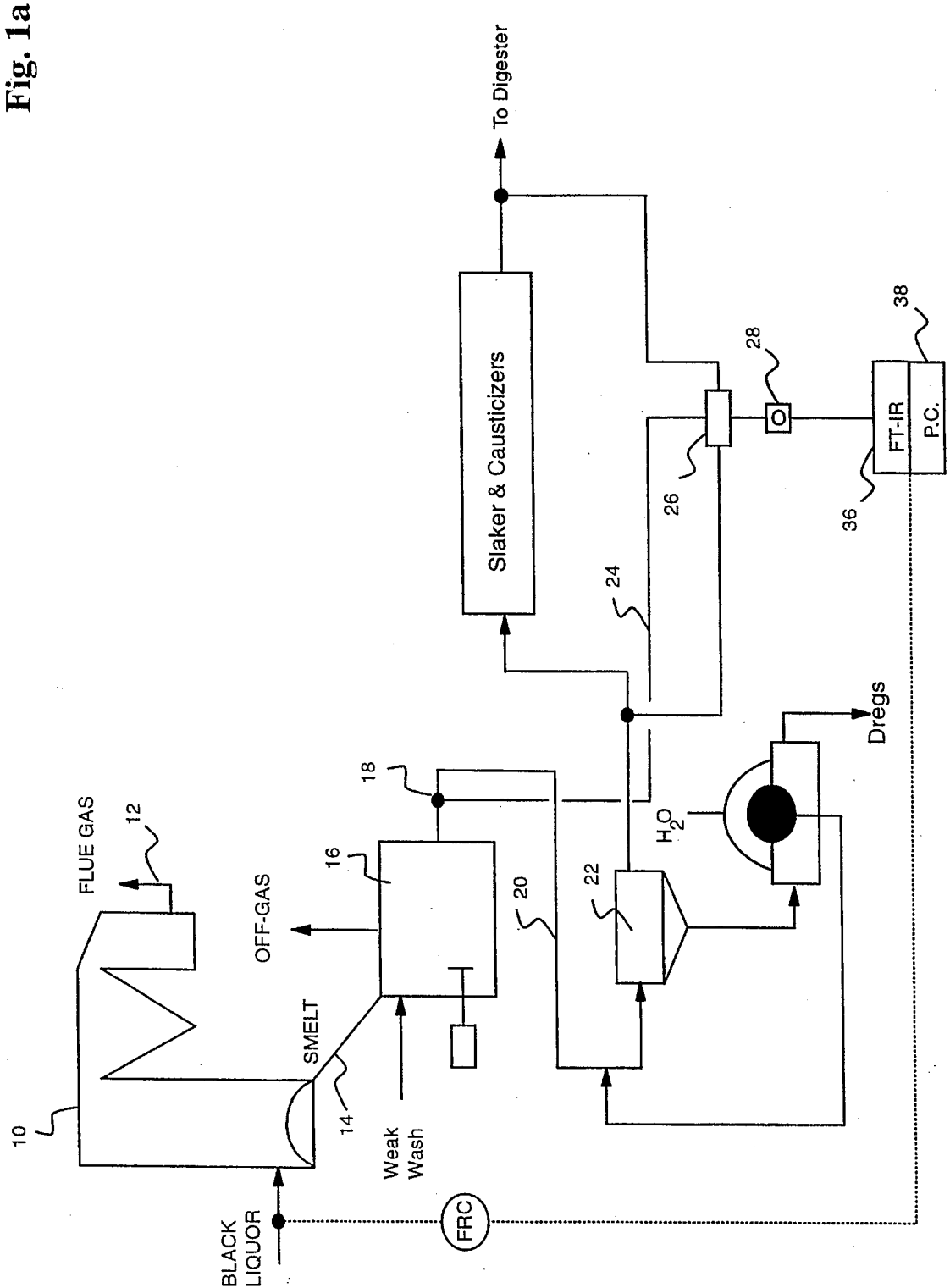
FIG. 1A is a diagrammatic view of a recovery system, complete with sensing apparatus according to one embodiment of the present invention.

FIG. 1A is a diagrammatic view of a recovery system, complete with sensing apparatus according to one embodiment of the present invention. Referring to FIG. 1A, black liquor passes through multiple-effect evaporators (not shown) and is admitted to the recovery furnace 10 to generate flue gases 12 and smelt 14. The smelt 14 flows to the smelt dissolving tank 16 to form a smelt solution which comprises green liquor. Green liquor samples are taken at sample withdrawing point 18 in line 20 leading to the green liquor clarifier 22. The samples are fed through a small-bore conduit 24 into a stream sampler 26 which contains either a transmittance-mode or reflectance-mode fiber-optic sensor 28, for which either mode is well-known in the art. As shown in FIG. 1B, the fiber-optic sensor 28 admits near-infrared light produced by the spectrometer 36 which exits from the illuminated outlet 30 of the fiber and which is made to propagate across the small liquor filled gap 32. The green liquor absorbs the near-infrared light across the gap 32, and the same light is collected at inlet 34 of the fiber. The infrared light collected from point 34 is then detected by the Fourier transform spectrometer 36. The spectrometer 36 records the near-infrared absorbance of the liquor. Readings from the spectrometer 36 are transferred to a computer 38 shown in FIG. 1A, which calculates the sodium sulfide concentration of the liquor and its sulfidity (on a TTA basis) with the use of a PLS multicomponent calibration model. Variations in the quantity of sodium hydroxide, sodium carbonate and sodium chloride coming into the smelt dissolving tank 16 have been accounted for by the calibration model, and therefore will not interfere with either the sulfide or the sulfidity measurements.

A combined system of pipes, light guides or infrared fiber-optic cables is used for remote sensing in the recovery system so that liquor can be sampled from multiple locations, thereby minimizing system costs by allowing multiple streams to be analysed by a single FT-IR apparatus. The computer can then be programmed so as to adjust the operational variables of the recovery furnace so that the efficiency of the reactions taking place in the lower furnace, i.e., the reduction of oxidized sulfur species such as sulfate and thiosulfate to sulfide, is improved. Alternatively, the information received from the computer may be communicated directly to an operator who will perform manual adjustments.

A Perkin-Elmer [Norwalk Conn.] 1610 FT-IR spectrometer was used for recording spectra. Spectra recorded were the result of 1024 averaged scans over a spectral range of 7800 cm$^{-1}$ (1.28 micrometers) to 5300 cm$^{-1}$ (1.89 micrometers) at a resolution of 16 cm$^{-1}$. The spectra were run at room temperature with the use of a 1.5 mm fused-silica transmission cell suitable for aqueous solutions. Absorbance spectra were collected against a background of air with the use of a transmission cell. A spectrum of either water or a caustic soda-sodium carbonate solution was subtracted from the liquor spectra so as to produce differential-absorbance spectra which reflect the amount and variety of ionic species present in solution. The PLS facility provided with the LabCalc™ (Galactic Industry Corp., Salem N.H.) data processing software package was used for the multicomponent calibration step.

Three series of synthetic-liquor mixtures were made with the use of reagent-grade chemicals. Five kraft-mill samples (Mills A, B, D, E, F) and one sulfite-mill sample (Mill C) were also obtained from separate locations. The composition of the samples contained in the first series of synthetic-liquor mixtures is given in Table I. Caustic soda and sodium carbonate were characterised as a single component because their spectral signatures could not be distinguished with the PLS calibration, those signatures being almost identical in the spectral region which is most highly correlated with concentration of these species.

Figure 2:
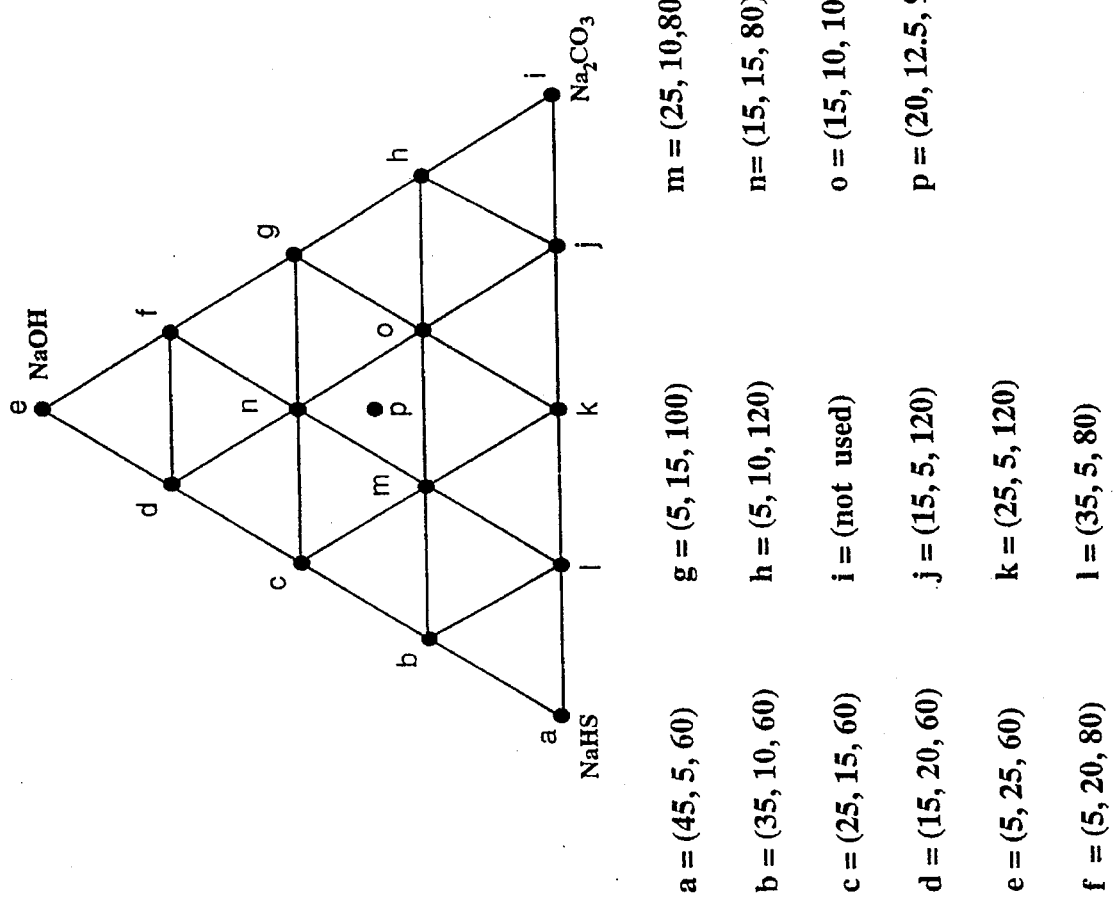
FIG. 2 is a ternary diagram illustrating the three-component semi-constrained mixture design for choosing the calibration samples used for building the two-component PLS calibration model.

FIG. 2 is a ternary diagram illustrating three-component (NaHS, NaOH, Na$_2$CO$_3$) design choosing the calibration samples used in the second series of synthetic-liquor samples for building the two-component (NaHS, NaOH+Na$_2$CO$_3$) PLS calibration model.

Figure 3:
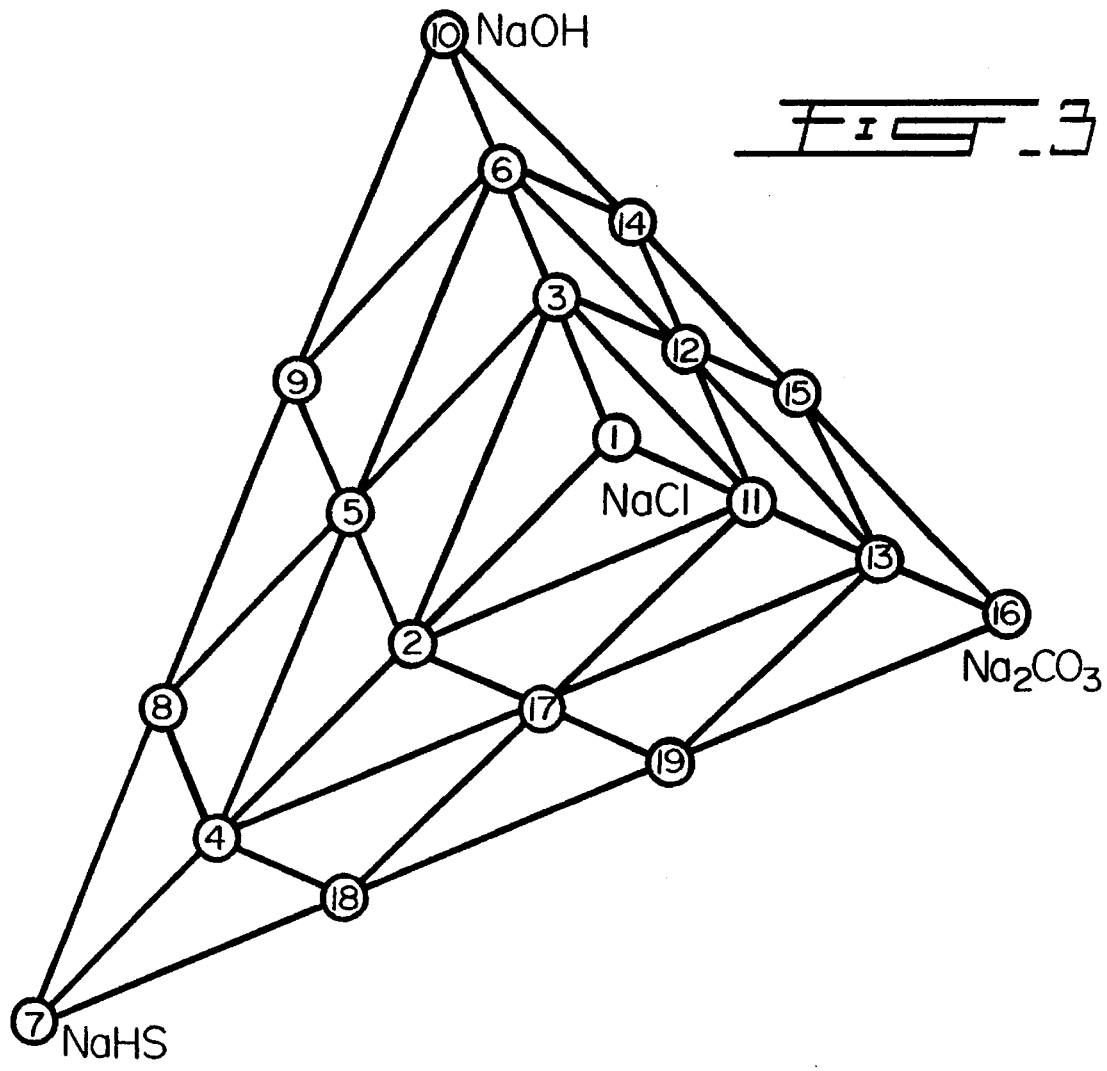
FIG. 3 is a quaternary diagram illustrating the four-component semi-constrained mixture design for choosing the calibration samples used for building the three-component PLS calibration model.

FIG. 3 is a quaternary diagram illustrating the four-component (NaHS, NaOH, Na$_2$CO$_3$, NaCl) design for choosing the calibration samples used in the third series of synthetic-liquor samples for building the three-component (NaHS, NaOH+Na$_2$CO$_3$, NaCl) PLS calibration model. The hidden face of the tetrahedron shown in FIG. 3 is a ternary diagram identical to that displayed in FIG. 2. Sample 20 is located on the center of the hidden face, whereas the four other samples are situated near the centroid of the tetrahedron.

Referring to FIG. 2 and FIG. 3, the composition of the last two series of synthetic-liquor mixtures was chosen with the help of a semi-constrained mixture design for which the concentrations of components are broadly distributed in the following order over a range: sodium sulfide, 10 to 100 g/L (as Na$_2$O) (sodium hydrosulfide, 5 to 50 g/L (as Na$_2$O)); sodium hydroxide, 5 to 26 g/L (as Na$_2$O); sodium carbonate, 40 to 120 g/L (as Na$_2$O); sodium chloride, 5 to 35 g/L (as NaCl). Concentrations for all samples are numerically given in the same order below each mixture diagram. All concentrations were verified with standard methods ["T624 os-68— Analysis of Soda and Sulphate White and Green Liquors", TAPPI Standard Methods, TAPPI PRESS, Atlanta; "J.12— Analysis of Sulphate Green and White Liquors", Standard Methods of the Technical Section of the CPPA, Montreal]. The samples listed in Table I were combined with the second series of samples and used for building the two-component model. For each calibration model, the synthetic-liquor spectra were sorted between two sets, a calibration set and a validation set. Two-thirds of the samples, including all samples which showed concentrations extremes, were incorporated into the calibration set being used for building the spectral model, thereby minimizing the likelihood of outliers. The remainder of the samples were used for verifying the accuracy of the model and validating the calibration. Combining the absorbance spectra, as well as the known concentrations of sulfide, caustic, carbonate and optionally chloride for each spectrum, each calibration set was created for the purpose of building a prediction model. An additional mill sample of green liquor was chosen at random and used in each calibration set, thereby ensuring portability of the two models. Results obtained with the use of these two calibration models for the mill and validation samples are given in Tables II and III, respectively. These results are discussed in the following examples:

EXAMPLE 1

Figure 4:
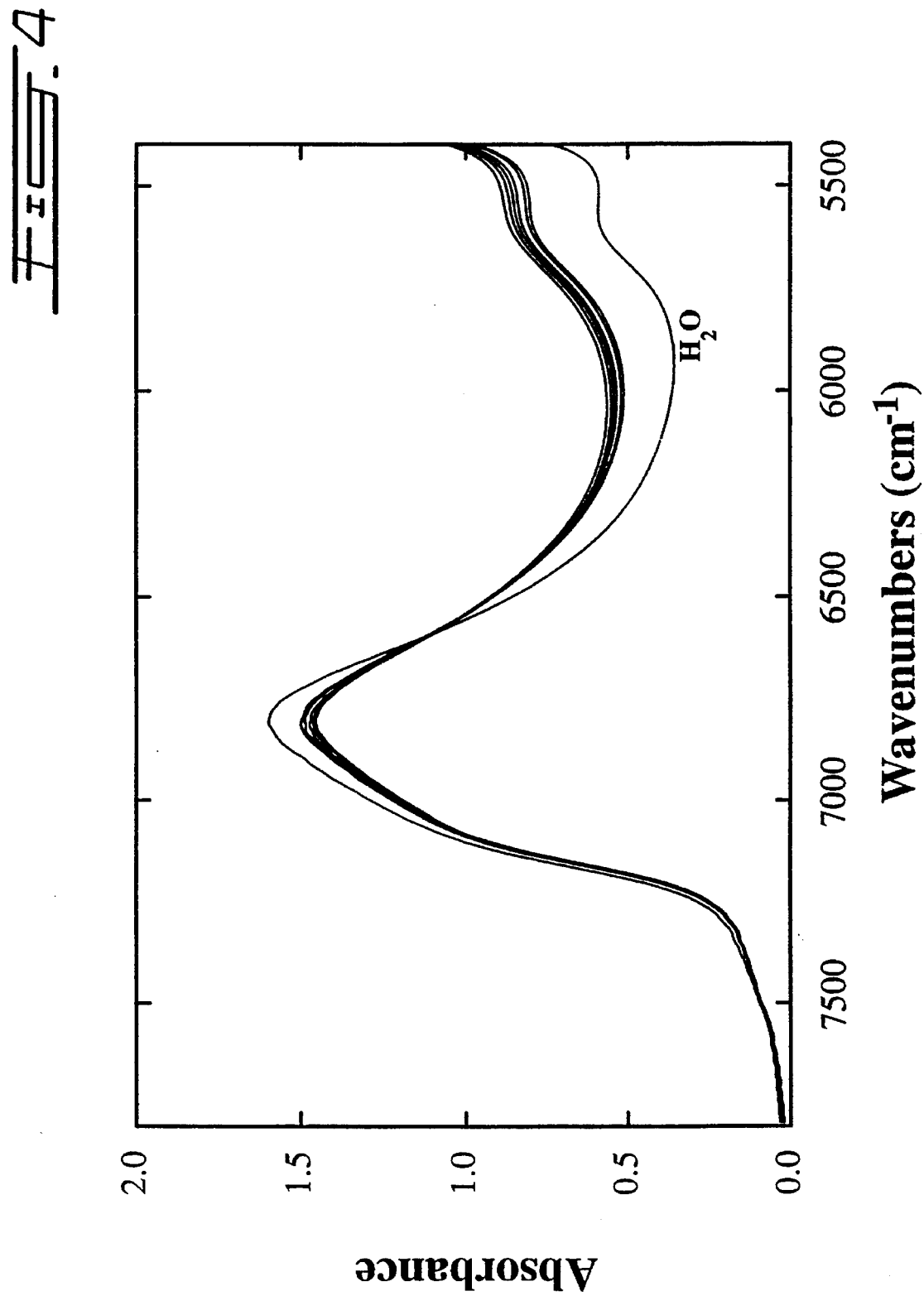
FIG. 4 is a graph of near-infrared absorbance versus wave numbers showing the change in the water-band absorbance with respect to an air reference spectrum for six synthetic green liquors having different sodium sulfide concentrations and a constant caustic and carbonate concentration.
Figure 5:
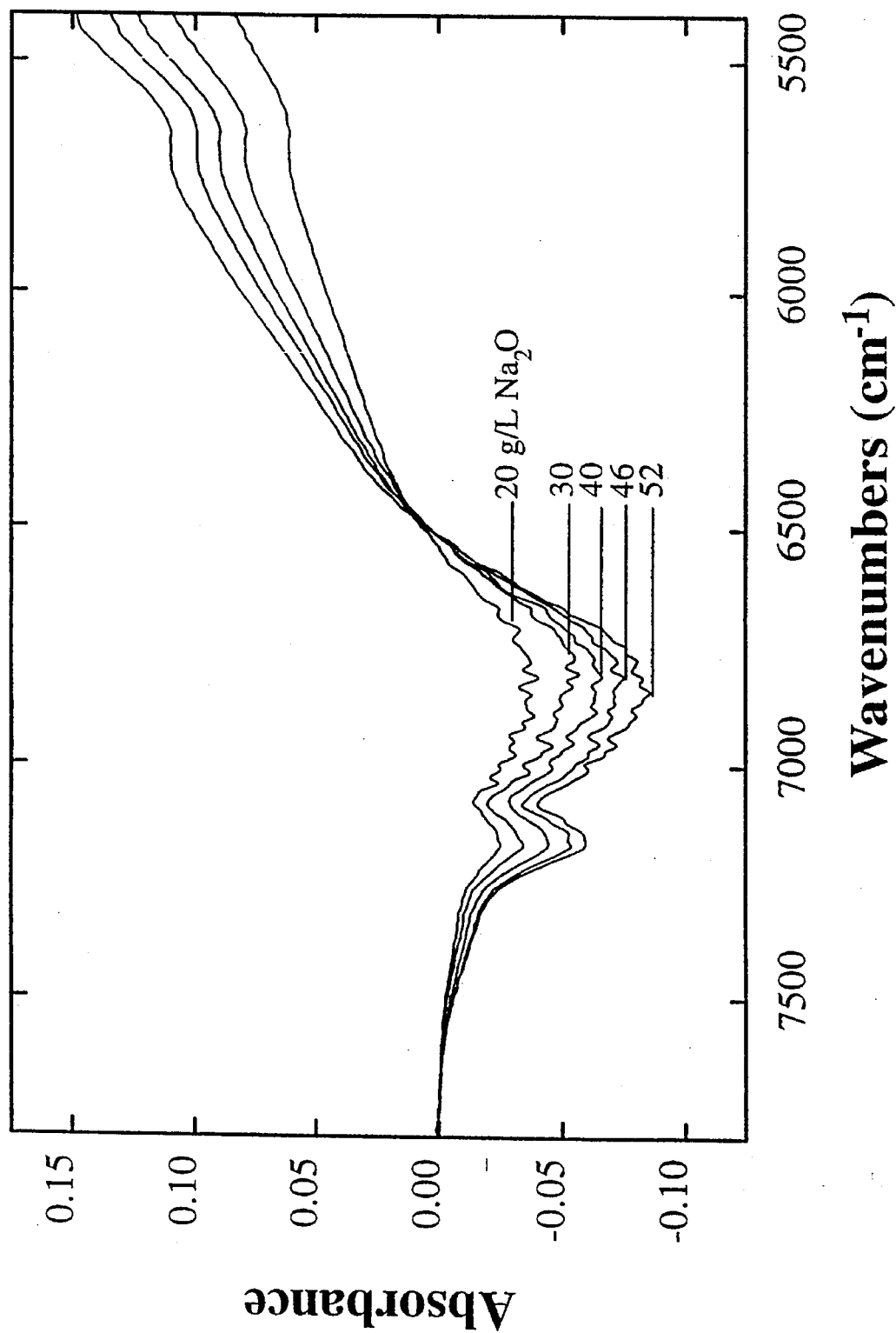
FIG. 5 is a graph of near-infrared differential absorbance versus wave numbers showing the change in the differential absorbance calculated with respect to a caustic soda-sodium carbonate reference spectrum for five synthetic green liquors having different sulfide concentrations.
Figure 6:
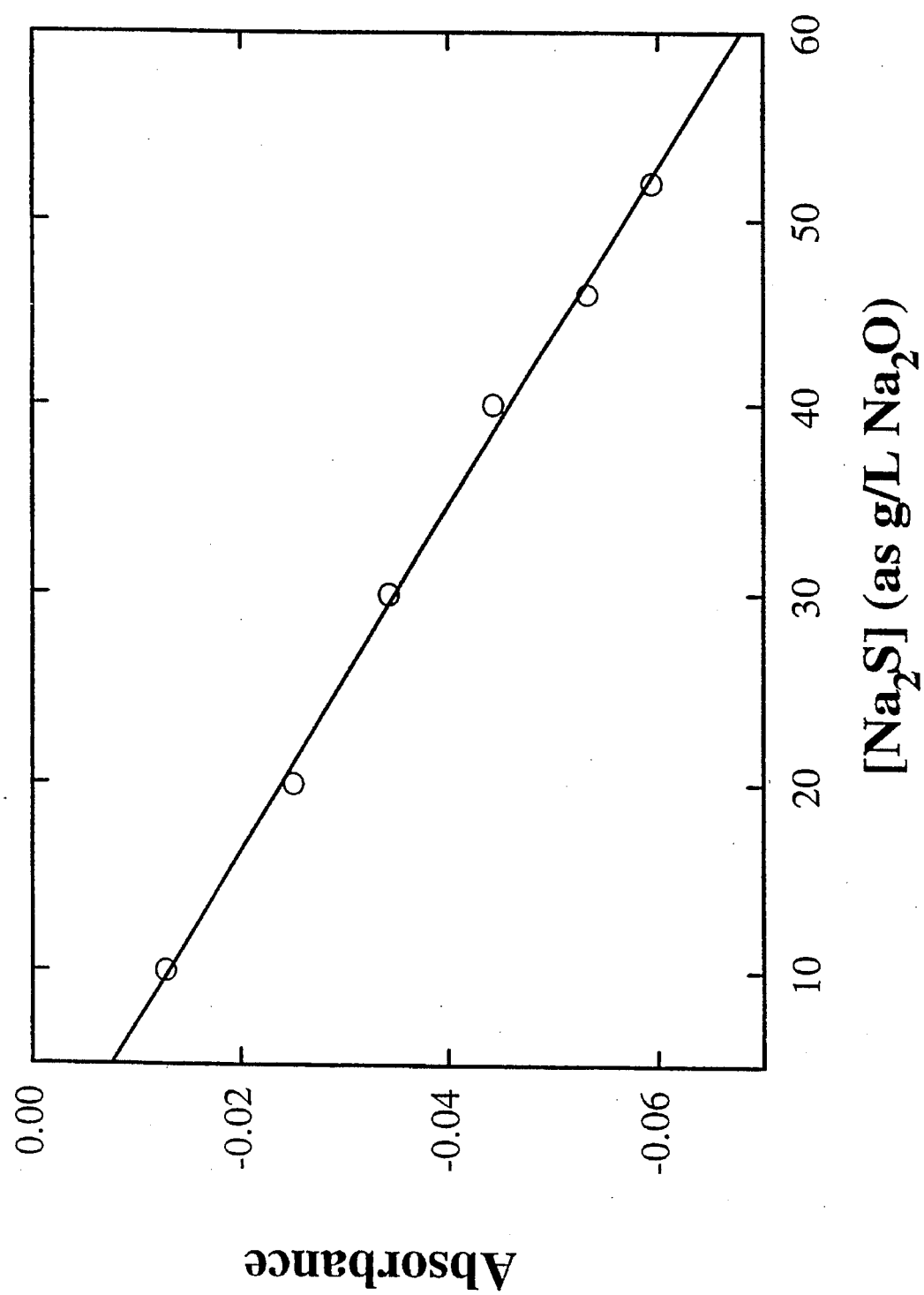
FIG. 6 is a calibration graph of the band absorbance at 7150 cm$^{-1}$ versus sodium sulfide concentration for six sodium sulfide concentrations.
Figure 7:
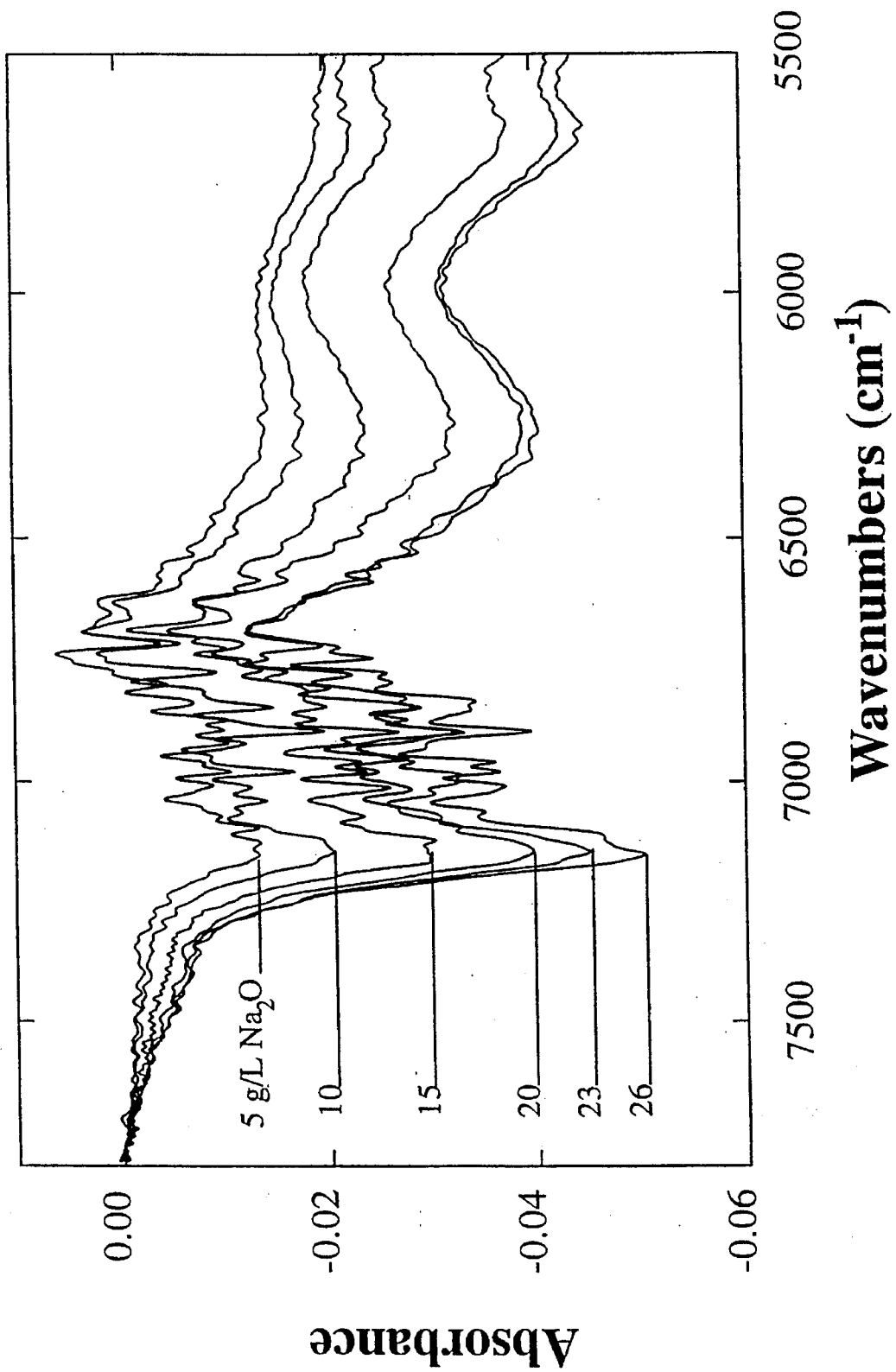
FIG. 7 is a graph of near-infrared differential absorbance versus wave numbers showing the change in the differential absorbance calculated with respect to an effective alkali-carbonate reference spectrum for six synthetic green liquors having different hydrosulfide concentrations.
Figure 8:
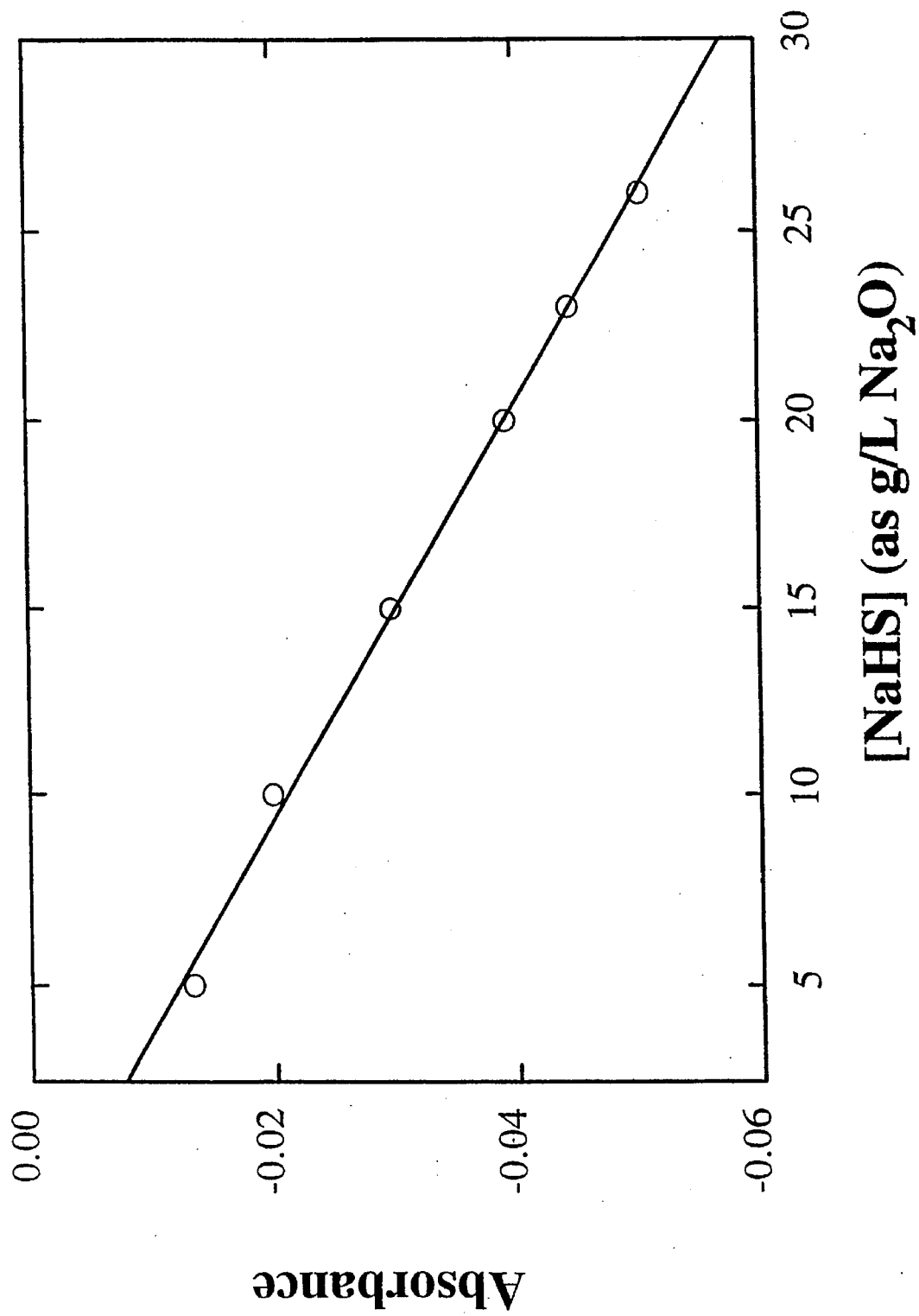
FIG. 8 is a calibration graph of the band absorbance at 7150 cm$^{-1}$ versus sodium hydrosulfide concentration for six sodium hydrosulfide concentrations.

The water-band absorption spectra for water and six synthetic green liquors (Na$_2$S: 10, 20, 30, 40, 46, 52 g/L (as Na$_2$O); NaOH : 12 g/L (as Na$_2$O); Na$_2$CO$_3$: 65 g/L (as Na$_2$O) shown in FIG. 4 demonstrate that the presence of sodium sulfide produces changes in water-band absorption which are correlated with sodium sulfide concentration. The differential-absorbance spectra shown in FIG. 5 were calculated with respect to a caustic soda-sodium carbonate (NaOH: 12 g/L (as Na$_2$O); Na$_2$CO$_3$: 65 g/L (as Na$_2$O) reference spectrum by subtracting the caustic soda-sodium carbonate spectrum from the spectra shown in FIG. 4. The absorption peak at a wavenumber of 7150 cm$^{-1}$ is linearly correlated with the sodium sulfide concentration, a trend which is clearly demonstrated in FIG. 6. So as to remove the hydroxide contribution present in the spectrum of sodium sulfide, differential-absorbance spectra were obtained with pure sodium hydroxide (NaOH: 5, 10, 15, 20, 23, 26 g/L (as Na$_2$O)) against a water reference spectrum, and subtracted from the spectra shown in FIG. 5. The resulting hydrosulfide spectra are shown in FIG. 7. Identical spectra are obtained if a series of effective alkali-sodium carbonate spectra are subtracted from the green-liquor spectra shown in FIG. 4. Although the spectral pattern for hydrosulfide seen in FIG. 7 is now very different from that shown in FIG. 5, the absorption peak at a wavenumber of 7150 cm$^{-1}$ still remains linearly correlated with the sodium hydrosulfide concentration, a trend which is clearly demonstrated in FIG. 8. These results also suggest that the NIR differential-absorption spectra for green liquors are excellent candidates for building a PLS calibration model.

EXAMPLE 2

Figure 9:
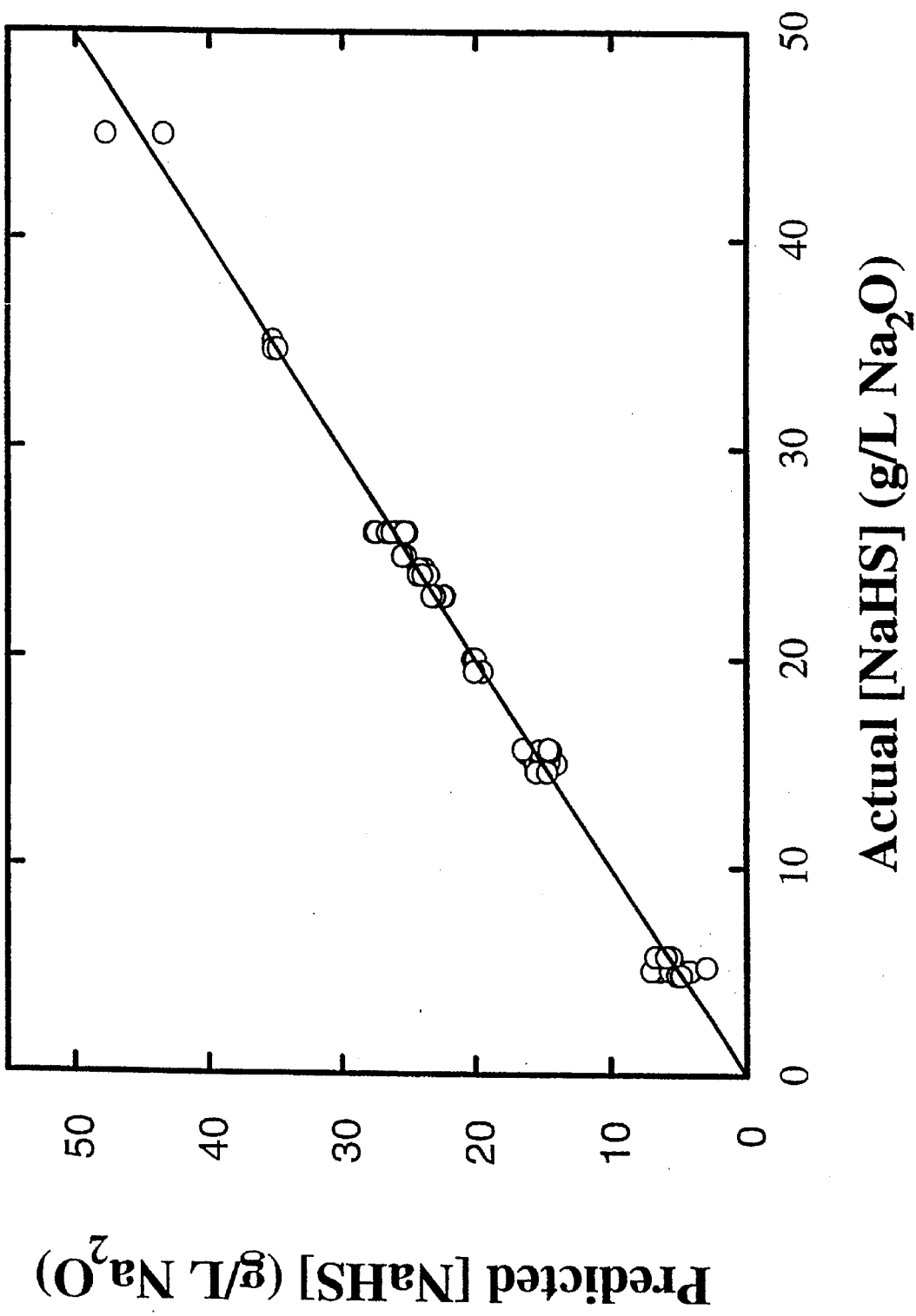
FIG. 9 is a PLS calibration graph of the predicted versus actual hydrosulfide concentration for the two-component PLS calibration model.
Figure 10:
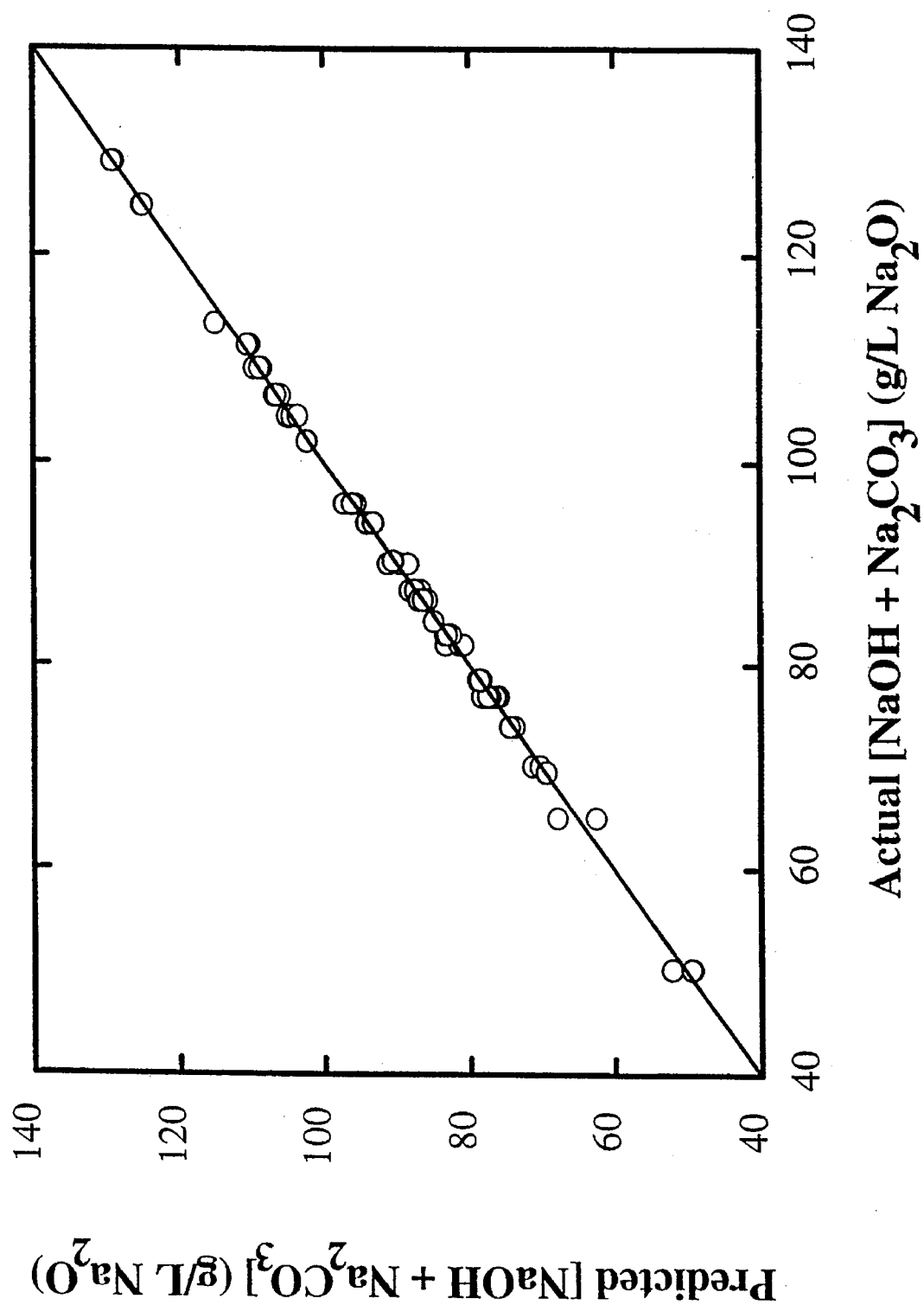
FIG. 10 is a PLS calibration graph of the predicted versus actual combined caustic soda-sodium carbonate concentration for the two-component PLS calibration model.

A two-component PLS calibration was performed on the set of synthetic samples listed in Table I and FIG. 2 for the purpose of building a calibration model that is capable of predicting 1) sodium sulfide concentrations and/or percent sulfidity, 2) TTA in green liquors and smelt solutions. The spectral regions chosen for building the model were as follows: 1) hydrosulfide, 3 regions: 5728–6060, 6744–6900 and 6930–7030 cm$^{-1}$; 2) caustic soda-sodium carbonate, 2 regions: 6116–6243 and 6400–6630 cm$^{-1}$. The calibration graph shown in FIG. 9 for hydrosulfide indicates that such a model can be built for hydrosulfide. The linear parameters for the calibration curve shown in FIG. 9 are: intercept, 0.004 g/L (as Na$_2$O); slope, 1.0034. Since the standard deviation on the intercept is 0.189, this translates into an error of about 0.2 g/L (as Na$_2$O) for hydrosulfide. The calibration plot for caustic soda and sodium carbonate shown in FIG. 10 also confirms that TTA can be measured, thereby leading to an accurate sulfidity measurement. The linear parameters for the calibration curve shown in FIG. 10 are: intercept, 0.102 g/L (as Na$_2$O); slope, 0.999. Since the standard deviation on the intercept for NaOH and sodium carbonate is 0.481 and the error on NaHS is 0.2, this translates into an error of about 0.7 g/L (as Na$_2$O) for TTA. The results shown in Table II for mill and validation samples show good agreement for both Na$_2$S and TTA concentrations between the near-infrared analysis and standard-method determinations. Preferred ranges for the chemical species under consideration are therefore: Na$_2$S, 20 to 100 g/L (as Na$_2$O); TTA, 105 to 140 g/L (as Na$_2$O).

EXAMPLE 3

Figure 11:
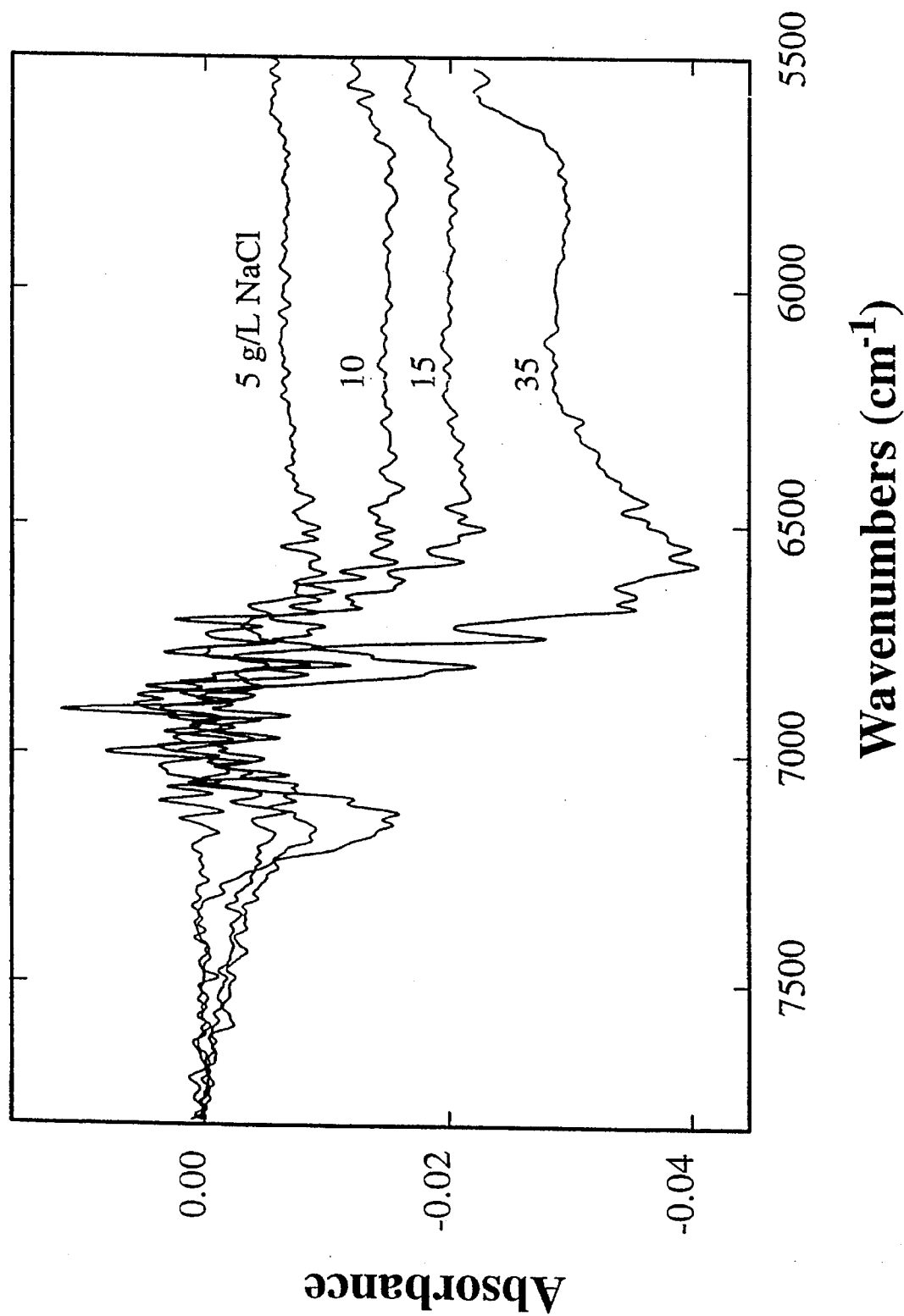
FIG. 11 is a graph of near-infrared differential absorbance versus wave numbers showing the change in the differential absorbance calculated with respect to a water reference spectrum for a synthetic green liquor having four different chloride concentrations.
Figure 12:
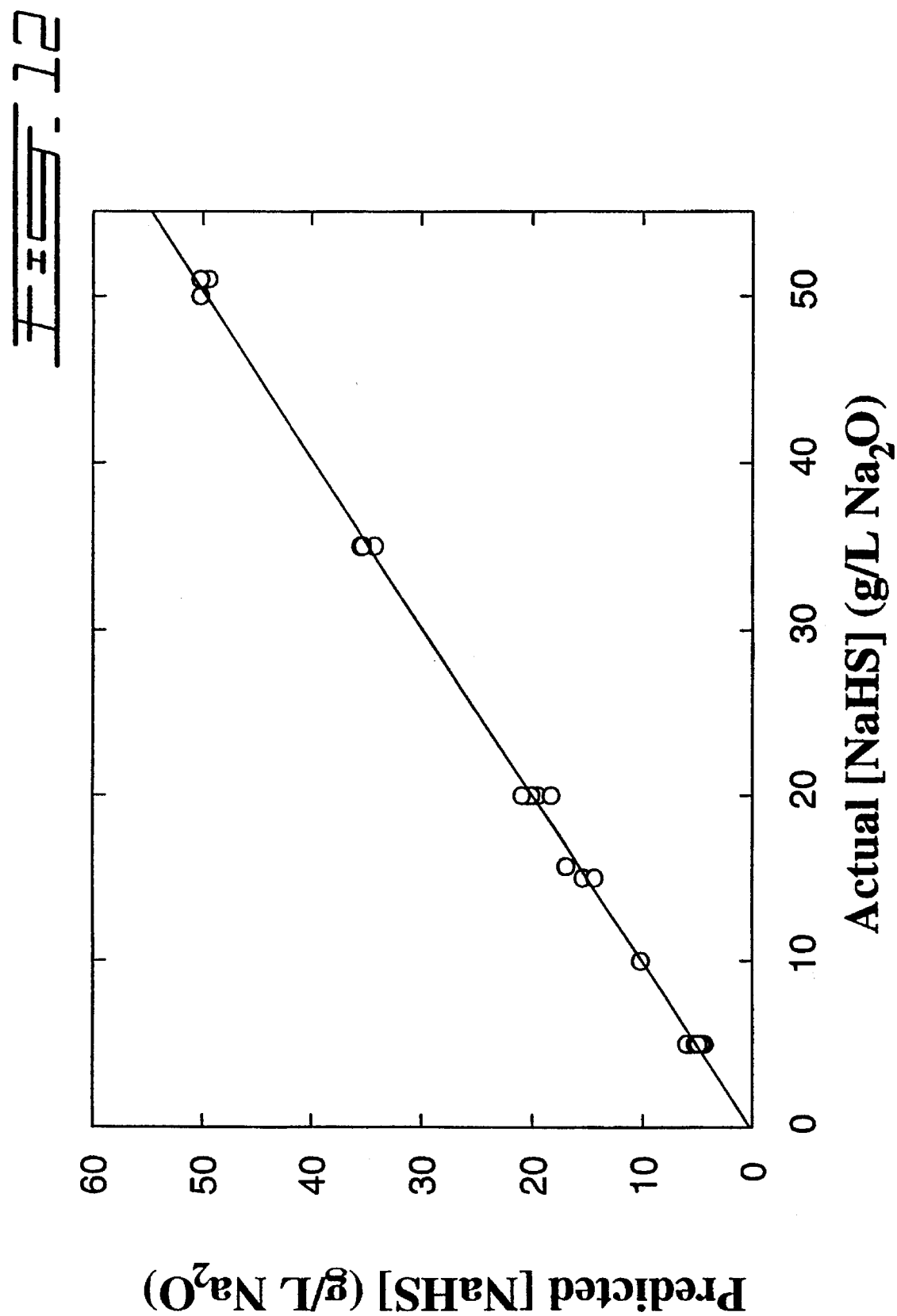
FIG. 12 is a PLS calibration graph of the predicted versus actual hydrosulfide concentration for the three-component PLS calibration model.
Figure 13:
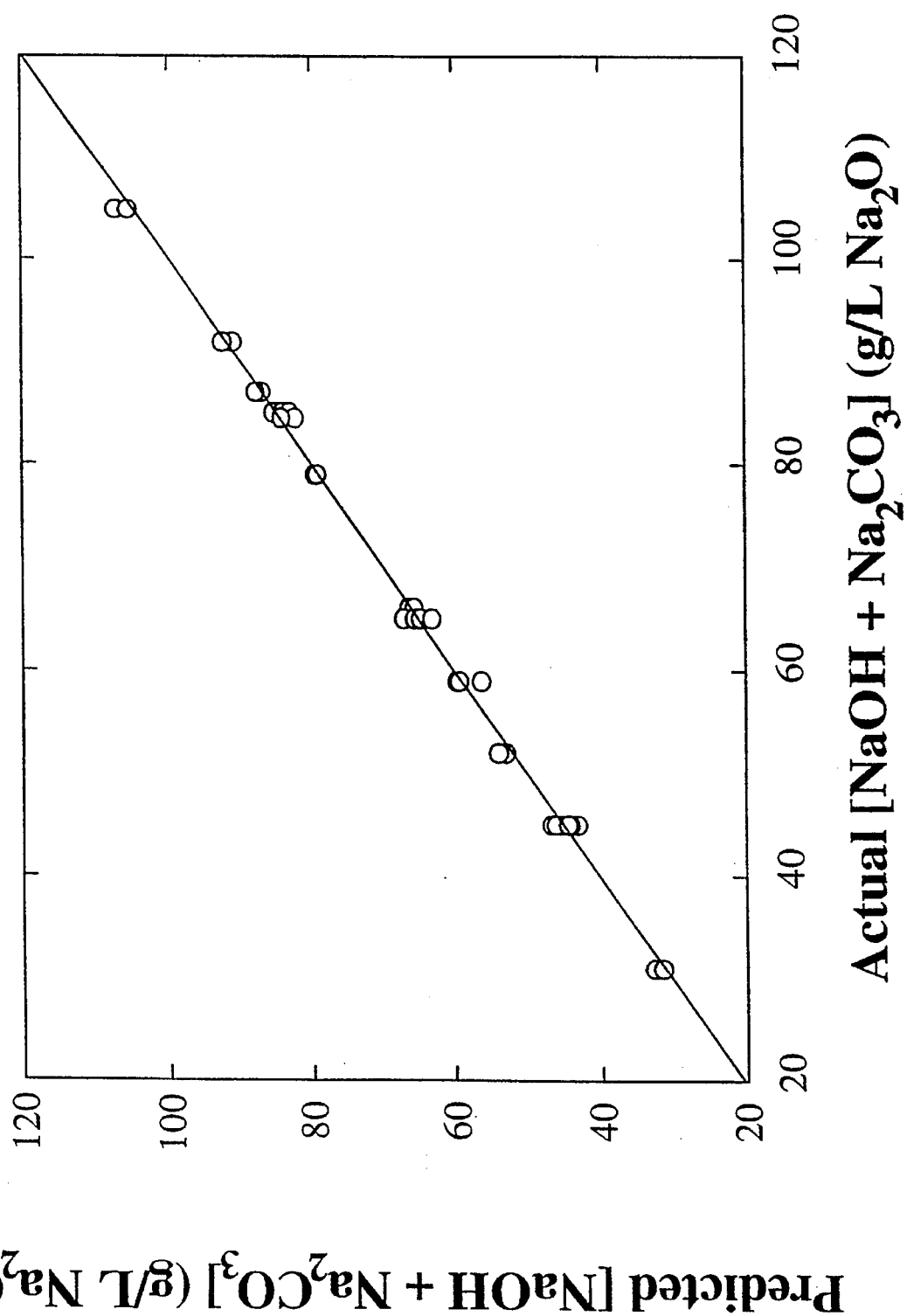
FIG. 13 is a PLS calibration graph of the predicted versus actual combined caustic soda-sodium carbonate concentration for the three-component PLS calibration model.
Figure 14:
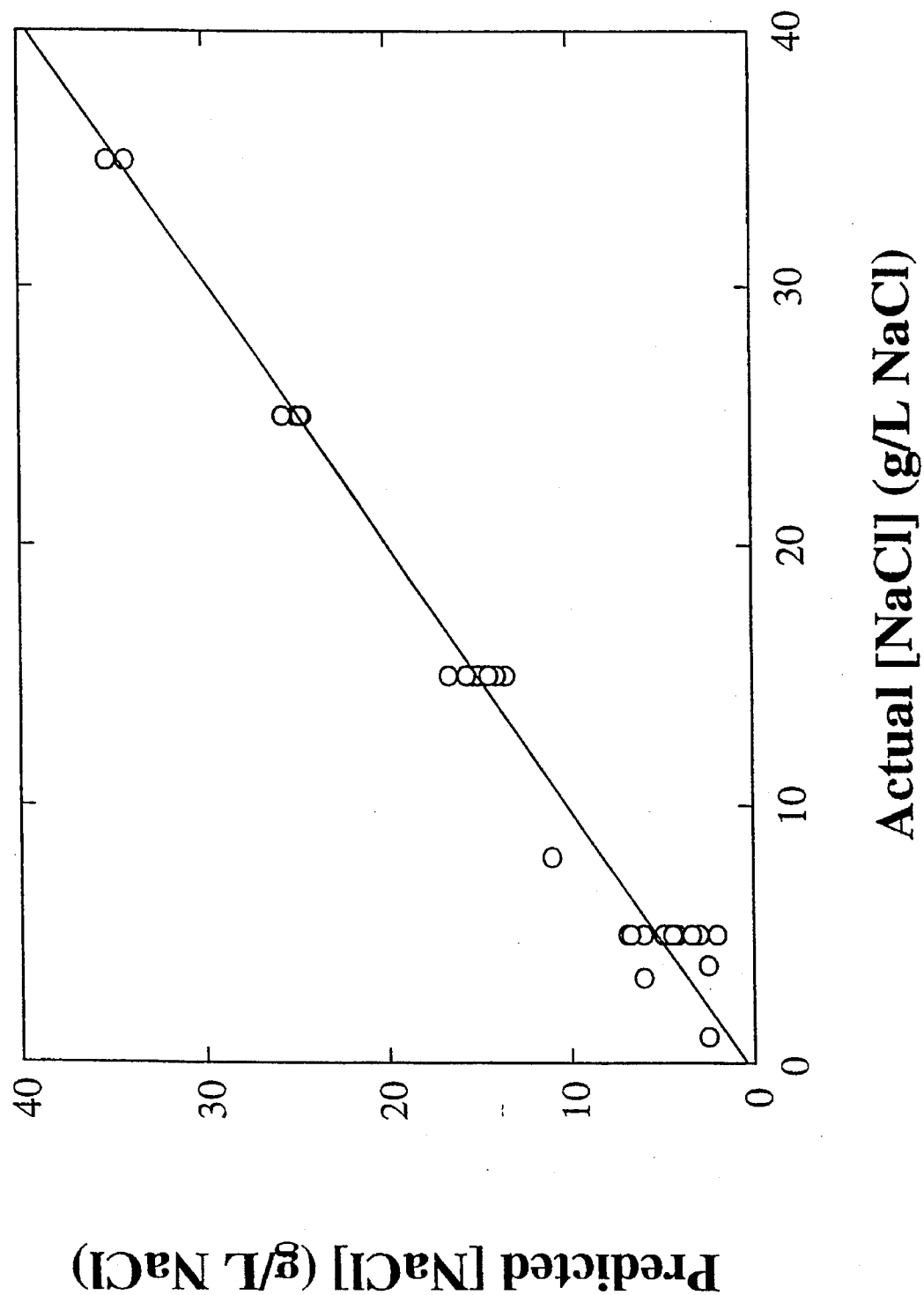
FIG. 14 is a PLS calibration graph of the predicted versus actual sodium chloride concentration for the three-component PLS calibration model.

The differential-absorbance spectra shown in FIG. 11 for sodium chloride were calculated with respect to a synthetic green liquor (Na$_2$S : 30 g/L (as Na$_2$O); NaOH : 10 g/L (as Na$_2$O); Na$_2$CO$_3$: 77 g/L (as Na$_2$O) reference spectrum by subtracting the green-liquor absorbance spectrum from the chloride-spiked green liquor spectra. The absorption peak at a wavenumber of 6600 cm$^{-1}$ is somewhat correlated with the sodium chloride concentration. A three-component PLS calibration was performed on the set of synthetic samples listed in FIG. 3 for the purpose of building a calibration model that is capable of predicting 1) sodium sulfide concentrations and/or percent sulfidity, 2) TTA and 3) chloride in green liquors and smelt solutions. The spectral regions chosen for building the model were as follows: 1) hydrosulfide, 2 regions: 7166–7553 and 6650–6725 cm$^{-1}$; 2) caustic soda-sodium carbonate, 1 region: 6449–6618 cm$^{-1}$ 3) chloride, 1 region: 5650–6400 cm$^{-1}$. The calibration graph shown in FIG. 12 for hydrosulfide indicates that such a model can be built for hydrosulfide. The linear parameters for the calibration curve shown in FIG. 12 are: intercept, 0.216 g/L (as $Na_2O$); slope, 0.989. Since the standard deviation on the intercept is 0.201, this translates into an error of about 0.2 g/L (as $Na_2O$) for hydrosulfide. The calibration plot for caustic soda and sodium carbonate shown in FIG. 13 confirms that TTA can still be measured, thereby leading to an accurate sulfidity measurement. The linear parameters for the calibration curve shown in FIG. 13 are: intercept, 0.514 g/L (as $Na_2O$); slope, 0.993. Since the standard deviation on the intercept for NaOH and sodium carbonate is 0.725 and the error on NaHS is 0.2, this translates into an error of about 0.92 g/L (as $Na_2O$) for TTA. The calibration plot for sodium chloride in FIG. 14 indicates that this parameter can be measured. The linear parameters for the calibration curve shown in FIG. 14 are: intercept, 0.406 g/L (as NaCl); slope, 0.977. The standard deviation on the intercept for chloride is 0.393 g/L (as NaCl) for chloride. The results shown in Table III for mill and validation samples show good agreement for $Na_2S$, TTA and chloride concentrations between the near-infrared analysis and standard-method determinations. The preferred concentration ranges for both $Na_2S$ and TTA are the same as that of the previous example whereas the preferred range for chloride is 10 to 25 g/L (as NaCl).

From the above examples it can be seen that different types of green liquors and smelt solutions in either the kraft or sulfite pulping process can be analysed and that the sodium sulfide content, the sulfidity (based on TTA) and optionally the sodium chloride content of liquors can be measured with the use of various types of partial least-squares (PLS) multivariate calibration which correlate the spectral behavior for different concentrations of each component in a calibration sample with their actual concentration in that sample. The set of correlations represents a model which can then be used to predict the concentration of sodium sulfide and/or sulfidity (based on TTA), and optionally sodium chloride in an unknown sample. Consequently, by varying at least one process variable, the process can be controlled so that optimal values of the aforesaid parameters are obtained.

Various changes may be made to the embodiments shown herein without departing from the scope of the present invention which is limited only by the following claims.

TABLE I

Compositions[1] of synthetic green liquor samples used for the two-component PLS calibration

| Sample No. | $Na_2S$ (g/L $Na_2O$) | $Na_2CO_3$ + NaOH (g/L $Na_2O$) | TTA[2] (g/L as $Na_2O$) |
|---|---|---|---|
| 1 | 10.0 | 77.0 | 87.0 |
| 2 | 20.0 | 77.0 | 97.0 |
| 3 | 30.0 | 77.0 | 107.0 |
| 4 | 40.0 | 77.0 | 117.0 |
| 5 | 46.0 | 77.0 | 126.0 |
| 6 | 52.0 | 77.0 | 129.0 |
| 7 | 10.0 | 50.2 | 60.2 |
| 8 | 52.0 | 50.2 | 102.2 |
| 9 | 52.0 | 90.2 | 142.2 |
| 10 | 10.0 | 90.2 | 100.2 |
| 11 | 31.0 | 70.2 | 101.2 |
| 12 | 10.0 | 74.0 | 84.0 |
| 13 | 52.0 | 74.0 | 126.0 |
| 14 | 52.0 | 114.0 | 166.0 |
| 15 | 10.0 | 114.0 | 124.0 |
| 16 | 31.0 | 94.0 | 125.0 |
| 17 | 31.0 | 102.1 | 133.1 |
| 18 | 31.0 | 62.1 | 93.1 |
| 19 | 10.0 | 82.1 | 92.1 |
| 20 | 52.0 | 82.1 | 134.1 |
| 21 | 31.0 | 82.1 | 113.1 |

[1] by CPPA J.12 standard procedure or by TAPPI T624 os-68 standard procedure
[2] TTA = $Na_2S$ + NaOH + $Na_2CO_3$

TABLE II

Comparison of results from the two-component PLS calibration with standard chemical analyses[1] for mill green liquor samples and synthetic validation samples

| | $Na_2S$ (g/L, as $Na_2O$) | | $Na_2CO_3$ + NaOH (g/L, as $Na_2O$) | | TTA[2] (g/L, as $Na_2O$) | |
|---|---|---|---|---|---|---|
| SAMPLE | NIR | CHEMICAL ANALYSIS | NIR | CHEMICAL ANALYSIS | NIR | CHEMICAL ANALYSIS |
| MILL-A | 28.6 | 30.4 | 88.4 | 87.3 | 117.0 | 117.7 |
| MILL-B | 29.8 | 29.9 | 80.2 | 79.6 | 110.0 | 109.5 |
| MILL-C | 101.4 | 102.2 | 31.9 | 31.4 | 133.3 | 133.6 |
| MILL-D | 34.4 | 34.3 | 72.8 | 75.5 | 107.2 | 109.8 |
| MILL-E | 24.4 | 23.6 | 88.9 | 91.1 | 113.3 | 114.7 |
| VAL-1 | 54.0 | 52.0 | 49.9 | 50.2 | 103.9 | 102.2 |
| VAL-2 | 11.3 | 10.0 | 72.7 | 74.0 | 85.3 | 84.0 |
| VAL-3 | 31.0 | 31.0 | 63.6 | 62.1 | 94.6 | 93.1 |
| VAL-4 | 30.7 | 31.0 | 82.1 | 83.8 | 112.8 | 114.8 |
| VAL-5 | 39.5 | 40.0 | 76.4 | 77.0 | 115.9 | 117.0 |
| VAL-6 | 51.7 | 52.0 | 77.1 | 77.0 | 128.8 | 129.0 |

[1] by CPPA J.12 standard procedure or by TAPPI T624 os-68 standard procedure
[2] TTA = $Na_2S$ + NaOH + $Na_2CO_3$

TABLE III

Comparison of results from the three-component PLS calibration with standard chemical analyses[1] for mill green liquor samples and synthetic validation samples

| SAMPLE | $Na_2S$ (g/L, as $Na_2O$) | | $Na_2CO_3$ + NaOH (g/L, as $Na_2O$) | | TTA[2] (g/L, as $Na_2O$) | |
| --- | --- | --- | --- | --- | --- | --- |
| | NIR | CHEMICAL ANALYSIS | NIR | CHEMICAL ANALYSIS | NIR | CHEMICAL ANALYSIS |
| MILL-A | 30.4 | 30.4 | 88.4 | 87.3 | 3.2 | 2.5 |
| MILL-B | 29.8 | 29.9 | 80.2 | 79.6 | 7.4 | 6.8 |
| MILL-C | 101.2 | 102.2 | 31.9 | 31.4 | 3.2 | 3.3 |
| MILL-D | 34.0 | 34.3 | 72.8 | 75.5 | 5.9 | 2.9 |
| VAL-1 | 10.2 | 10.0 | 52.4 | 52.0 | 24.8 | 25.0 |
| VAL-2 | 70.4 | 70.0 | 51.3 | 52.0 | 5.6 | 5.0 |
| VAL-3 | 8.4 | 10.0 | 72.4 | 72.0 | 15.7 | 15.0 |
| VAL-4 | 38.2 | 40.0 | 72.0 | 72.0 | 5.5 | 5 |

[1]by J.12 standard procedure or by TAPPI T624 os-68 standard procedure

I claim:

1. A method for determining a sulfur concentration parameter of sulfide-containing aqueous pulp green liquor comprising:
   i) subjecting a sample of the aqueous pulp green liquor to near infrared radiation at a wavelength region of wave number of 5300 to 7800 $cm^{-1}$ to produce a water absorbance peak value of said liquor, relative to a background spectrum
   ii) comparing the peak value in i) with a calibration plot of corresponding peak values at said wavelength region, for a plurality of sulfide-containing aqueous pulp liquors of known sulfur concentration parameters, and
   iii) evaluating the sulfur concentration parameter of the sample from the comparison in ii),
   wherein said green liquor sample in i) is fed from a green liquor preparation unit of a pulp manufacture process, said unit including a recovery furnace for chemicals derived from the pulp manufacture process and in which the green liquor is derived from a smelt of inorganic chemicals from said recovery furnace, and including a step of:
   iv) controlling operation of the recovery furnace in response to the evaluation of the sulfur concentration parameter in iii) to adjust the sulfur concentration parameter of the green liquor.

2. A method according to claim 1 wherein said concentration parameter is sulfide concentration.

3. A method according to claim 1 wherein said concentration parameter is percent sulfidity.

4. A method according to 1 wherein the background spectrum is a water sulfidity.

5. A method according to claim 1 wherein the background spectrum is a caustic soda-sodium carbonate solution spectra.

6. A method for determining the concentration of sodium sulfide in green liquors and smelt solutions derived from the preparation of kraft or sulfite pulp wherein smelt is produced in a recovery furnace and fed to a smelt dissolving tank so as to form green liquor, which comprises the steps of:
   withdrawing samples of a smelt solution or green liquor from the kraft or sulfite manufacturing process;
   subjecting the undiluted samples to near-infrared spectrophotometry over the range of wave numbers from 4000 to 14000 $cm^{-1}$ so as to produce absorbance measurements relative to a reference spectrum of water or a caustic soda-sodium carbonate solution;
   determining the absorbance shown by different mixture solutions of sodium sulfide, sodium hydroxide, sodium carbonate and sodium chloride of known concentrations;
   correlating by multivariate calibration the relationships between the absorbance measurements of the samples and the absorbance shown by the different mixture solutions of known concentration, and
   evaluating from the correlation the amount of sodium sulfide for any level of total titratable alkali (TTA) or chloride present in the liquor.

7. The method according to claim 6 wherein the near-infrared absorbance measurements are carried out within the range of wave numbers from 5300 to 7800 $cm^{-1}$.

8. The method according to claim 6, for determining the sulfidity (TTA basis) of the smelt solution or green liquor, wherein the caustic soda, sodium carbonate is also determined and the percent sulfidity is calculated from the data obtained, wherein the combined concentration of caustic soda and sodium carbonate are also determined by measuring the near-infrared absorbance of the undiluted smelt solution or undiluted green liquor.

9. The method according to claim 7 for determining the sulfidity on a TTA basis of the green liquor, wherein the caustic soda, sodium carbonate and chloride are also determined and the percent sulfidity is calculated from the data obtained, wherein the combined concentration of caustic soda, sodium carbonate and chloride are determined by measuring the near infrared absorbance of undiluted green liquor.

10. The method according to claim 8 wherein the near-infrared absorbance measurements are carried out within the range of wave numbers from 5300 to 6700 $cm^{-1}$.

11. The method according to claim 9 wherein the near-infrared absorbance measurements are carried out within the range of wave numbers from 5300 to 6700 $cm^{-1}$.

12. The method according to claim 6 wherein the near-infrared spectrophotometry over the range of wave numbers from 4000 to 14000 $cm^{-1}$ is transmittance spectrophotometry.

13. The method according to claim 12 wherein the transmittance is from a fiber-optic transmittance cell.

14. The method according to claim 12 wherein the transmittance is from a reflectance cell.

15. The method according to claim 6 wherein the spectrophotometry is performed in a flow-through cell for continuous measurements.

16. The method according to claim 6 wherein the relationships between the absorbance measurements of samples with the absorbance for different sulfide concentrations obtained with a partial least-squares (PLS) multivariate calibration.

17. The method according to claim 1 wherein said calibration plot is a plot of peak absorbance v. sulfur concentration parameter developed by a partial least squares multicomponent calibration technique.

18. In a cellulosic pulp manufacturing installation having a green liquor preparation unit including a recovery furnace for chemicals derived from a pulp manufacture process, a green liquor generation tank and a smelt flow line for flow of a smelt of inorganic chemicals from said recovery furnace to said tank, the improvement comprising a sensing apparatus for determining a sulfur concentration parameter of said green liquor, said apparatus comprising a fiber optic sensor operatively connected to a source of near infrared radiation over the range of wave numbers from 4000 to 14000 $cm^{-1}$ a sample flow line from said tank, a sensing zone in said sample flow line for receiving near infrared radiation from said sensor, a spectrophotometer for recording absorbance spectra from said sensing zone, and comparator means for comparing the absorbance spectra from said sensing zone with a calibration of absorbance spectra for known concentration parameters and providing an evaluation of the concentration parameter of the sample.

19. An installation according to claim 18 further including control means for controlling operating parameters of said recovery furnace, said control means being operatively connected to said comparator means for adjustment of said operating parameters responsive to the evaluation provided by the comparator means.

20. An installation according to claim 19 wherein said source of near infrared radiation is over a range of 5300 to 7800 $cm^{-1}$.

* * * * *